United States Patent [19]

Ilvespää et al.

[11] 4,342,764
[45] Aug. 3, 1982

[54] GUANIDINE COMPOUNDS, PHARMACEUTICAL COMPOSITIONS AND USE

[75] Inventors: Atso Ilvespää, Allschwil; Jörg Frei, Hölstein; Ernst Schweizer, Arlesheim, all of Switzerland

[73] Assignee: Ciba-Geigy Corporation, Ardsley, N.Y.

[21] Appl. No.: 151,031

[22] Filed: May 19, 1980

[30] Foreign Application Priority Data

May 29, 1979 [CH] Switzerland .......................... 4995/79

[51] Int. Cl.³ .................. A61K 31/535; A61K 31/42; C07D 413/12; C07D 261/04
[52] U.S. Cl. ............................ 424/248.56; 424/246; 424/248.52; 424/248.53; 424/248.55; 424/250; 424/267; 424/272; 544/58.7; 544/60; 544/62; 544/137; 544/367; 546/197; 546/209; 548/244; 548/246; 260/245.5
[58] Field of Search ................ 544/137, 367, 60, 58.7, 544/62; 546/197, 209; 548/244, 246; 260/245.5; 424/246, 248.52, 248.53, 248.55, 248.56, 250, 267, 272

[56] References Cited

U.S. PATENT DOCUMENTS 2,762,815 9/1956 Pohland .............................. 548/246
4,250,173 2/1981 Cantello ............................. 424/246

Primary Examiner—Robert W. Ramsuer
Attorney, Agent, or Firm—Michael W. Glynn

[57] ABSTRACT

The invention relates to guanidine derivatives, particularly to substituted guanidines of the formula

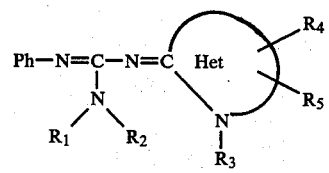

(I)

having hypoglycaemic activity, for the oral treatment of hyperglycaemia in mammals, especially for the oral treatment of Diabetes mellitus.

13 Claims, No Drawings

GUANIDINE COMPOUNDS, PHARMACEUTICAL COMPOSITIONS AND USE

The invention relates to novel guanidine derivatives and also to processes for their preparation and to pharmaceutical preparations which contain these novel compounds and to the use thereof.

The invention relates to novel guanidine derivatives, especially heterocyclically substituted guanidines of the formula

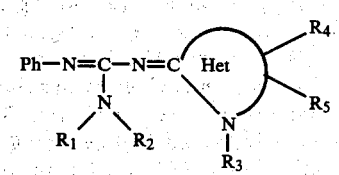

in which $R_1$ is a substituted or unsubstituted aliphatic or cycloaliphatic hydrocarbon radical and $R_2$ is hydrogen or substituted or unsubstituted aliphatic hydrocarbon radical, or $R_1$ and $R_2$ taken together are a substituted or unsubstituted divalent hydrocarbon radical of aliphatic character, in which the carbon atoms of the chain can be interrupted by a heteroatom, $R_3$ is hydrogen or lower alkyl, $R_4$ is hydrogen, lower alkyl, lower alkoxy, lower alkylthio, lower alkylamino, di-lower alkylamino, halogen, trifluormethyl or substituted or unsubstituted phenyl or, on a carbon atom which has single bonds on both sides, also oxo, $R_5$ is hydrogen or lower alkyl, Het is a heteroalkylene radical having 3 chain members which with the group C-N makes up a heterocyclic five-membered ring which has 2 to 3 hetero-atoms form the group comprising oxygen, sulfur or nitrogen in the ring and can be unsaturated, and Ph ist a substituted or unsubstituted phenyl radical, and their tautomeric compounds and salts.

In this specification the term "lower" used to qualify radicals and compounds denotes that these contain preferably not more than 7 and in particular not more than 4 carbon atoms.

An aliphatic hydrocarbon radical $R_1$ or $R_2$, which can be substituted, is in particular an alkyl radical or an alkenyl or alkynyl radical, especially a lower alkyl radical or lower alkenyl or lower alkynyl radical. Substituents of aliphatic hydrocarbon radicals are, for example, free, esterified or etherified hydroxyl groups, such as lower alkanoyloxy, lower alkoxy or lower alkenyloxy groups, or halogen atoms, and also free or esterified carboxyl groups, such as lower alkoxycarbonyl.

In this specification the general terms can have the following meaning:

Lower alkyl groups are, for example, preferably methyl groups and also ethyl, n-propyl, isopropyl, n-butyl, isobutyl, sec.-butyl, tert.-butyl, n-pentyl, isopentyl, neopentyl, n-hexyl, isohexyl or n-heptyl groups; lower alkenyl groups are, for example, the allyl group or the 2-methylallyl group and lower alkynyl groups are preferably propargyl groups. Substituted lower alkyl groups are, for example, the trifluoromethyl group or a free or esterified carboxymethyl group, for example a lower alkoxycarbonylmethyl group, for example a methoxycarbonylmethyl group.

Lower alkoxy is, for example, methoxy, ethoxy, n-propoxy, isopropoxy, n-butoxy or n-pentyloxy and lower alkenyloxy is for example, vinyloxy or allyloxy.

Halogen atoms are in particular fluorine, chlorine or bromine atoms, but can also be iodine atoms.

A cycloaliphatic hydrocarbon radical which can be substituted by a lower alkyl radical is in particular a monocyclic, or also a polycyclic, cycloalkyl radical having, for example, not more than 12 and preferably 3 to 10 ring carbon atoms.

A cycloalkyl group is, for example, a cyclopropyl, cyclobutyl, cyclopentyl, cyclohexyl, cycloheptyl or adamantyl group.

A phenyl radical which may be substituted can be substituted by one, two or three identical or different substituents. Such substituents are, for example, hydrocarbon radicals, such as lower aliphatic hydrocarbon radicals, for example lower alkyl, free or functionally modified hydroxyl or mercapto, such as etherified hydroxyl, for example lower alkoxy, lower alkenyloxy or lower alkylenedioxy, and also lower alkylthio, or halogen, as substituted lower alkyl trifluoromethyl, nitro, amino including substituted amino, for example lower alkylamino or di-lower alkylamino, and free or functionally modified carboxyl, such as esterified carboxyl, for example lower alkoxycarbonyl.

Lower alkylthio is in particular methylthio and also ethylthio, isopropylthio, n-propylthio or straightchain or branched butylthio. Lower alkylamino or dilower alkylamino is, for example, methylamino, dimethylamino, ethylamino, diethylamino, n-propylamino, di-n-propylamino, isopropylamino, di-isopropylamino or n-butylamino or di-n-butylamino.

The two substituents $R_1$ and $R_2$ taken together can be a substituted or unsubstituted divalent aliphatic hydrocarbon radical having 4-7 carbon atoms in the chain. The group $-NR_1R_2$ is, for example, lower alkyleneamino in which the lower alkylene chain can, for example, be interrupted by a hetero-atom, for example oxygen, sulfur or nitrogen substituted by lower alkyl, lower alkoxy or phenyl or unsubstituted, and is, as lower alkyleneamino, for example pyrrolidino, 2,5-dimethylpyrrolidino, piperidino, 2-methylpiperidino, hexahydroazepino or octahydroazocino, as oxa-lower alkyleneamino, for example morpholino, as thia-lower alkyleneamino, for example thiomorpholino, or aza-lower alkyleneamino, for example piperazino or N-methyl- or N-phenyl-piperazino.

The heteroalkylene radical Het having 3 chain members, which together with the group C-N makes up a heterocyclic five-membered ring which has 2-3 heteroatoms form the group comprising oxygen, sulfur or nitrogen in the ring and can be unsaturated, forms, together with C-N, for example an imidazoline, imidazolidine, oxazoline, oxazolidine, thiazoline, thazolidine, isoxazoline, isoxazolidine, isothiazoline, isothiazolidine, 1,2,4-oxadiazoline, 1,2,4-oxadiazolidine, 1,3,4-oxadiazoline, 1,3,4-oxadiazolidine, 1,2,4-thiazoline, 1,2,4-thiazolidine, 1,3,4-thiazoline, 1,3,4-thiazolidine, pyrazoline, pyrazolidine, 1,2,3-triazoline, 1,2,3-triazolidine, 1,2,4-triazoline or 1,2,4-triazolidine ring.

Particularly preferred rings are the 4-imidazoline, imidazolidine, 4-oxazoline, oxazolidine, 4-thiazoline, thiazolidine, 4-(1,3,4)-thiadiazoline, 4-(1,3,4)-oxadiazoline, isoxazoline or isoxazolidine ring.

The novel compounds of the general formula I and their addition salts with inorganic or organic acids possess valuable pharmacological properties, in particular a hypoglycaemic activity, as can be shown on rats with a normal metabolism, after oral administration of doses of from 3 mg/kg, and also on rats in which a diabetes-like metabolic condition has been induced by the injection of streptozotocin [c.f. A. Junod et al., Proc. Soc. Exp. Biol. Med. 126, 201–205 (1967)]. The lowering of the blood sugar level is not accompanied by hyperlactataemia. The pharmacological findings characterise the novel compounds of the general formula I and their pharmaceutically acceptable acid addition salts as antidiabetic agents which can be used for the oral treatment of hyperglycaemia in mammals and in particular of diabetes mellitus.

Particularly the invention relates to novel guanidine derivatives, especially heterocyclically substituted guanidines of the formula:

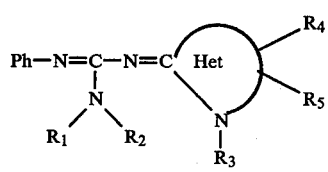

(I)

in which $R_1$ is lower alkyl or cycloalkyl and $R_2$ is hydrogen or lower alkyl, or $R_1$ and $R_2$ taken together are a lower alkylene chain which can be interrupted by an oxygen or sulfur atom or by a nitrogen atom which can be be substituted, for example by lower alkyl or phenyl, $R_3$ is hydrogen or lower alkyl, $R_4$ is hydrogen, lower alkyl, lower alkoxy, lower alkylthio, lower alkylamino, di-lower alkylamino, halogen, trifluoromethyl, or, on a carbon atom which has single bonds on both sides, also oxo, or phenyl which is unsubstituted or substituted by lower alkyl, lower alkoxy or halogen, $R_5$ is hydrogen or lower alkyl and Het is a heteroalkylene radical having 3 chain members, which with the group C-N makes up a saturated or mono-unsaturated heterocyclic five-membered ring having 2–3 hetero-atoms in the ring, and Ph is a substituted or unsubstituted phenyl radical, and also their tautomeric compounds and salts.

The invention relates especially to those compounds of the formula I in which $R_1$ is lower alkyl or cycloalkyl and $R_2$ is hydrogen or lower alkyl, or $R_1$ and $R_2$ taken together are a lower alkylene chain, which can be interrupted by an oxygen or sulfur atom or by a nitrogen atom which can be substituted, for example by lower alkyl or phenyl, as lower alkyleneamino, for example pyrrolidino, 2,5-dimethylpyrrolidino, piperidino, 2-methylpiperidino, hexahydroazepino or octahydroazocino, as oxalower alkyleneamino, for example morpholino, thia-lower alkyleneamino, for example thiomorpholino, or as aza-lower alkyleneamino, for example piperazino or N-methyl or N-phenyl-piperazino, $R_3$ is hydrogen or lower alkyl, $R_4$ is hydrogen, lower alkyl, lower alkoxy, lower alkyl thio, lower alkylamino, di-lower alkylamino, halogen, trifluormethyl or, on a carbon atom which has single bonds on both sides, also oxo, or phenyl which is unsubstituted or substituted by lower alkyl, lower alkoxy or halogen, $R_5$ is hydrogen or lower alkyl and Het is as divalent radical having 3 chain members, which with the group C-N makes up a saturated or mono-unsaturated heterocyclic five-membered ring having 2–3 hetero-atoms in the ring and can be, for example, an imidazoline, imidazolidine, oxazoline, oxazolidine, thiazoline, thiazolidine, isoxazoline, isoxazolidine, isothiazoline, isothiazolidine, oxadiazoline, oxadiazolidine, thiadiazoline, thiadiazolidine, pyrazoline, pyrazolidine or triazoline ring, and Ph is a phenyl radical which is unsubstituted or substituted by lower alkyl, lower alkoxy or halogen, and also their tautomeric compounds and salts.

Compounds of particular interest are those of the formula I in which $R_1$ is lower alkyl or cycloalkyl and $R_2$ is hydrogen or lower alkyl, or the group $-NR_1R_2$ is, as lower alkyleneamino, in which the lower alkylene chain can be interrupted by an oxygen or sulfur atom, and can be, for example, pyrrolidino, 2,5-dimethylpyrrolidino, piperidino, 2-methylpiperidino or morpholino, $R_3$ is hydrogen or lower alkyl, $R_4$ is hydrogen, lower alkyl, lower alkoxy, lower alkylthio, halogen, trifluoromethyl or, on a carbon atom which has single bonds on both sides, also oxo, or phenyl which is unsubstituted or substituted by lower alkyl, lower alkoxy or halogen, $R_5$ is hydrogen or lower alkyl and Het, as a divalent radical, together with the group C-N is a heterocyclic five-membered ring which can be mono-unsaturated, for example an imidazoline, imidazolidine, oxazoline, oxazolidine, thiazoline, thiazolidine, oxadiazoline, oxadiazolidine, triazoline, thiadiazoline or thiadiazolidine ring, and Ph is a phenyl radical which is unsubstituted or substituted by lower alkyl, lower alkoxy or halogen, and also their tautomeric compounds ans salts.

Compounds of very particular interest are those of the formula I in which $R_1$ is lower alkyl, for example methyl or ethyl, and $R_2$ is hydrogen or lower alkyl, for example methyl or ethyl, or the group $-NR_1R_2$, as lower alkyleneamino which can be interrupted by an oxygen or sulfur atom, is, for example, in the form of pyrrolidino, piperidino or morpholino, $R_3$ is hydrogen or lower alkyl, for example methyl or ethyl, $R_4$ is hydrogen, lower alkyl, for example methyl or ethyl, lower alkoxy, for example methoxy or ethoxy, lower alkylthio, for example methylthio or ethylthio, halogen, for example chlorine or bromine, trifluoromethyl or phenyl which is unsubstituted or substituted by lower alkyl, for example methyl or ethyl, or halogen, for example chlorine or bromine, $R_5$ is hydrogen or lower alkyl, for example methyl or ethyl, and Het, as a divalent heteroalkylene radical is, together with the group C-N, a heterocyclic five-membered ring which can be mono-unsaturated, for example the 4-imidazoline, 4-oxazoline, 4-oxazoline, 4-thiazoline, 4-(1,3,4)-thiadiazoline, 4-(1,3,4)-oxadiazoline or isoxazolidine ring, and Ph is a phenyl radical which is unsubstituted or substituted by lower alkyl, for example methyl or ethyl, halogen, for example chlorine or bromine, or lower alkoxy, for example methoxy or ethoxy, and also their tautomeric compounds and salts.

The novel guanidines of the formula I are obtained by methods known per se.

Thus, for example, the novel compounds of the formula I can be obtained by reacting a compound of the formula II

(II)

in which $X_1$ is the group Ph—N=, in which Ph is a substituted or unsubstituted phenyl radical, or a detachable group, $X_2$ is the group

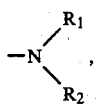

in which $R_1$ and $R_2$ are as defined under formula I, or a detachable group and $X_3$ is the group

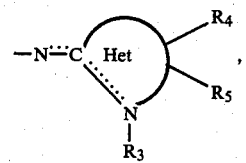

in which $R_3$, $R_4$, $R_5$ and Het, as a divalent heteroalkylene radical with the group C-N, are as defined under formula I, or a detachable group, with the proviso that only one of the substituents $X_1$, $X_2$, or $X_3$ can be a detachable group, and one of the groups $X_1$, $X_2$ or $X_3$ is bound by a double bond to a carbon atom, with an amine or imine which is identical to the missing amino or imino group, which are defined under $X_1$, $X_2$ or $X_3$, in order to replace the detachable group, and, if desired, carrying out additional process steps and/or, if desired, converting resulting compounds of formula I into a salt and/or, if desired, converting resulting salts of compounds of the formula I into free bases.

Detachable groups $X_1$, $X_2$ and $X_3$ are, for example, lower alkylthio groups, for example methylthio or ethylthio, lower alkoxy, for example methoxy or ethoxy, or halogen, for example chlorine or bromine.

Depending on whether the detachable group is $X_1$, $X_2$ or $X_3$, compounds of the general formula II are either compounds of the formula IIa:

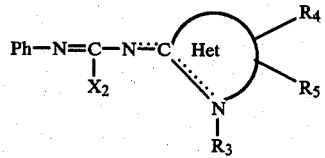

(IIa)

in which $X_2$ is a detachable group and Ph, $R_3$, $R_4$, $R_5$ and Het and C-N are as defined above, compounds of the general formula IIb:

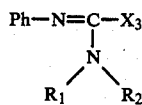

(IIb)

in which $X_3$ is a detachable group, or compounds of the formula IIc

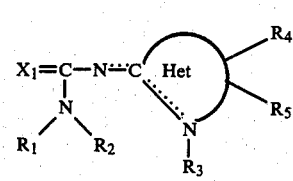

(IIc)

in which $X_1$ is a detachable group, or the tautomeric forms or acid addition salts thereof.

Depending on whether $X_1$, $X_2$ or $X_3$ is present as the detachable group in a compound of the formula II, a compound of the formula IIa is reacted with an amine of the formula $HNR_1R_2$, a compound of the formula IIb is reacted with an imino compound of the formula III:

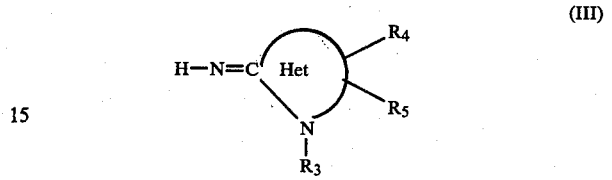

(III)

or a compound of the formula IIc is reacted with a substituted or unsubstituted aniline of the formula Ph-$NH_2$. Compounds of the formulae IIa, IIb and IIc can also be used in the form of acid addition salts, preferably in the form of the halides. Analogously, the amines, imino compounds or anilines used can also be reacted in the form of acid addition salts, preferably in the form of the halides.

The reaction of a compound of the formula II, i.e. a compound of the formula IIa, IIb or IIc, for example with an above mentioned amine or imine in the form of the free base, is carried out using a stoichiometric excess of the amine or imine, for example in a molar ratio of 1:1.05 to 1:2.0. If only a slight excess of the amine or imine in the form of the free base is used or if the amine or imine is used in the form of an acid addition salt, it is preferable to add an additional stoichiometrically equivalent amount of a tertiary alkylamine, for example triethylamine or N-ethyldiisopropylamine.

If, for example, an imino compound of the formula III is reacted in the form of the free base

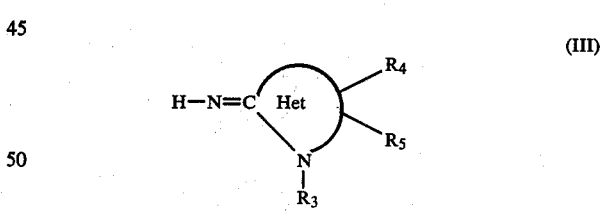

(III)

with a compound of the formula IIb in which $X_3$ is a halogen, preferably 2 mol equivalents or more of the free base of the abovementioned imino compound are used. In accordance with the following reaction equation

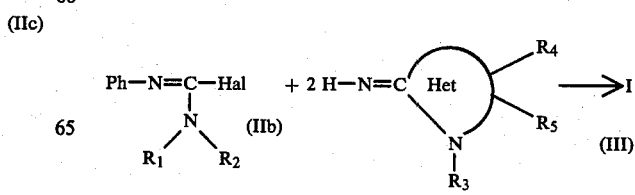

-continued

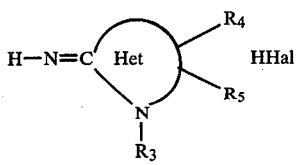

one equivalent of the imino compound in the form of the acid addition salt is formed. For this reason, the reaction is preferably carried out in an aprotic solvent in which the resulting compound of the formula I is soluble but the addition salt of the hydrogen halide acid according to the above reaction pattern precipitates as an insoluble compound. In this way, the two reaction products obtained can easily be separated from one another by simple filtration. The resulting acid addition salt of the imino compound is converted to the free base by basic hydrolysis, for example by the addition of an alkali metal hydroxide or carbonate or alkaline earth metal hydroxide or carbonate, and can thus be recovered as starting material for re-use. Preferably, however, compounds of the formula IIb and III are reacted in the form of acid addition salts, for example in the form of the halides, as indicated above in the presence of an additional tertiary alkylamine, for example triethylamine or N-ethyldiisopropylamine.

The reactions of compounds of the formula IIb with an imino compound of the formula III which have been described are, as already mentioned, preferably carried out in aprotic solvents. Examples of solvents which can preferably be used are ethers, for example diethyl ether and tetrahydrofuran, lower aliphatic ketones and esters, for example acetone, methyl ethyl ketone and ethyl acetate, aromatic hydrocarbons, for example benzene, toluene or xylene, and acetonitrile. Particularly preferentially, however, the reaction is carried out in diethyl ether or acetonitrile. The reactions can be carried out at a temperature between 0° and 150° C., but preferably between room temperature and the reflux temperature of the reaction mixture.

If, however, the starting compound of the formula II which is used is, for example, a compound of the formula IIa:

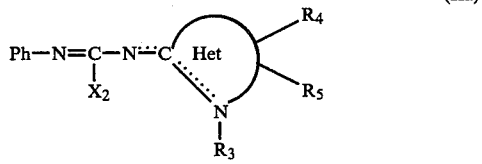

(IIa)

$X_2$, as the detachable group, is preferably a lower alkoxy or lower alkylthio group. Starting compounds of the formula IIa are reacted in the form of their salts, for example in the form of their acid addition salts with a hydrogen halide acid, with an amine of the formula $HNR_1R_2$ in the form of the free base, in which $R_1$ and $R_2$ are as defined above.

The reactions are carried out, for example, in an alcohol as the solvent, preferably in a lower alkanol, for example isopropanol or tert.-butanol, at temperatures from room temperature up to, preferably, the reflux temperature of the reaction mixture. The reactions can, however, be carried out in a closed reaction vessel under pressure, for example in a bomb tube or in an autoclave, at higher temperatures. The guanidine derivatives of the general formula I are obtained in the form of their salts and these can be converted to the corresponding free bases, for example by alkaline hydrolysis. In the case of the reaction of compounds of the general formula IIa with the amine of the general formula $HNR_1R_2$, the amine is preferably used in a stoichiometric excess, for example in a molar ratio of 1:1.05 to 1:2.0 and above. If only a slight excess of the amine is used it can be appropriate to add an additional stoichiometrically equivalent amount of a tertiary alkylamine, for example triethylamine or N-ethyl-diisopropylamine, in order to increase the rate of reaction.

The reactions of compounds of the formula IIc containing a detachable group $X_1$, which, as well as a halogen atom, is preferably lower alkoxy or lower alkylthio, or of such compounds in a tautomeric form, with a substituted or unsubstituted aniline in the form of the free base are carried out in the same way as has been described for the reaction of a compound of the formula IIa with an amine of the formula $HNR_1R_2$. The reactions are advantageously also carried out in a stoichiometric excess of the substituted or unsubstituted anilines. If only a slight excess of the aniline is used, it can be appropriate to add an additional stoichiometrically equivalent amount of one of the tertiary trialkylamines already defined above.

Compounds of the general formula I can also be prepared by reacting a guanidine compound of the general formula IV:

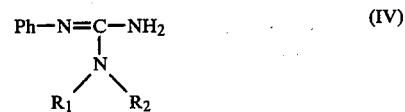

(IV)

in which Ph, $R_1$ and $R_2$ are as defined under formula I, with a compound of the general formula V:

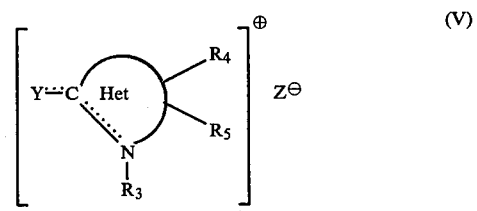

(V)

in which Y is lower alkoxy, for example methoxy or ethoxy, lower alkylthio, for example methylthio or ethylthio, or halogen, for example chlorine or bromine, or Y is two lower alkoxy groups located on the same C atom, and Z is a tetrafluoborate anion, a fluorosulfonate anion, a lower alkylsulfate anion, such as a methylsulfate anion, or an alkanesulfonate anion, for example a methanesulfonate anion, or a halide, for example chloride or bromide, and, if Y is two lower alkoxy groups on the same C atom, there is no anion Z, or, if $R_3$ is hydrogen, the tautomeric form is present as the free base, and, if desired, carrying out additional process steps and/or, if desired, converting resulting compounds of the formula I into a salt and/or, if desired, converting resulting salts of compounds of the formula I into free bases.

The compounds of the general formula I are appropriately prepared by reacting a lactam salt of the formula IV indicated above with a guanidine derivative of the formula IV defined above, in stoichiometric amounts. The reactions are preferably carried out in an anhydrous organic solvent. Organic solvents are, for example, lower alkanols, for example methanol, ethanol, isopropanol or tert.-butanol, ethers, for example diethyl ether, tetrahydrofuran or dioxan, lower halogenated hydrocarbons, for example chloroform, methylene chloride or 1,2-dichloroethane, and aromatic hydrocarbons, for example benzene, toluene or xylene. In general, the reaction is carried out at temperatures which are between −20° C. and +50° C., but preferably between 0° C. and room temperature.

The reaction product of the general formula I, which is obtained in the form of a salt, is converted to the free base by basic hydrolysis, for example by the addition of an alkali metal hydroxide or carbonate or alkaline earth metal hydroxide or carbonate.

The lactam fluoborates or lactam fluorosulfonates of the general formula V which are employed according to the process and in which $Z^-$ is a tetrafluoborate group of the formula $BF_4^-$ or a fluorosulfonate group of the formula $OSO_2F^-$ can be prepared by conventional processes, by reacting a lactam of the formula Va:

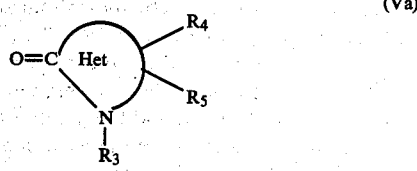

(Va)

with the corresponding trialkyloxonium fluoborate or a lower alkyl fluorosulfonate to give the corresponding lactam salt of the general formula V.

The reaction is carried out, for example, at temperatures between −20° C. and +50° C., preferably at temperatures between 0° C. and +25° C., in an inert gas, for example nitrogen or argon, and in the presence of an inert, anhydrous organic solvent, for example in a lower halogenated hydrocarbon, for example chloroform, 1,2-dichloroethane or preferably methylene chloride. Examples of other organic solvents which can be used are ethers, for example diethyl ether, dioxan, tetrahydrofuran or 1,2-dimethoxyethane, and aromatic hydrocarbons, for example benzene, toluene or xylene.

The 2-lower alkylthiolactim ethers which fall under the general formula V can be prepared by reacting the lactam of the general formula Va with phosphorus pentasulfide by a procedure analogous to that according to R. Gomper et al., Org. Syn. Coll., volume V, pages 780–785. When this reaction is carried out, a thiolactam is first obtained and on reaction with an alkylating agent this yields the 2-alkylthiolactim ether in the form of the corresponding salts. Alkylating agents which can be used are an alkyl halide, for example methyl iodide, an alkyl fluorosulfonate, for example methyl fluorosulfonate, an alkyl methanesulfonate, for example methyl methanesulfonate, an alkyl toluenesulfonate, for example methyl toluenesulfonate, or dimethyl sulfate. The reaction of the lactim ether salts with the guanidine derivative of the general formula IV yields the corresponding salts of the general formula I.

When the lactam fluorosulfonates of the general formula V, which have been described above, are reacted with the guanidines of the general formula IV, quaternary ammonium salts of the general compounds of the general formula I can also form in a side reaction.

The methylsulfate salts, which also fall under the general formula V, are obtained by a procedure analogous to that described for pyrrolidones by H. Bredereck et al., Chem. Ber., volume 96, (1963), page 1350, form lactams of the general formula Va by reaction with dimethyl sulfate. The reaction is preferably carried out in an anhydrous, inert organic solvent, for example an aromatic hydrocarbon, for example benzene, toluene or xylene, an ether, for example diethyl ether, dioxan or tetrahydrofuran, or a halogenated aliphatic hydrocarbon, for example 1,2-dichloroethane or chloroform. The resulting methylsulfate of the general formula V is then converted with the corresponding guanidine derivative of the general formula IV in the manner described above to the corresponding lower alkyl-sulfate salt, for example the methylsulfate salt of the compound of the general formula I.

The resulting salts can be converted to corresponding free bases of the general formula I by treatment with an alkali metal hydroxide or carbonate or alkaline earth metal hydroxide or carbonate.

The corresponding lactam acetal of the formula Vb:

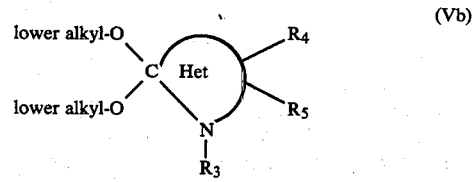

(Vb)

can be prepared form the lower alkyl-sulfate salt, for example the methyl-sulfate salt, of the general formula V, for example by reaction with a metal alkoxide, preferably an alkali metal alkoxide, for example sodium methoxide or sodium ethoxide, in the corresponding anhydrous lower alkanol.

As described above, the free bases of the general formula I can be prepared from the lactam acetals, with the guanidine derivatives of the general formula IV.

The halide salts, especially chloride salts, of the lactams of the general formula V which are used according to the process can be prepared in a manner analogous to that described for pyrrolidones by W. Jentsch and M. Seefelder, Chem. Ber., volume 98 (1965), page 274, by reacting a lactam of the general formula Va with phosgene or thionyl chloride.

As already mentioned above, the free bases of the general formula V can also be used for the preparation of the compounds of the general formula I in which $R_3$ is a hydrogen atom. The reaction of the salts of the general formula V with a base, for example an alkali metal hydroxide or carbonate or alkaline earth metal hydroxide or carbonate, preferably in a halogenated aliphatic hydrocarbon as the solvent, for example methylene chloride or chloroform, yields the free bases of the general formula Vc:

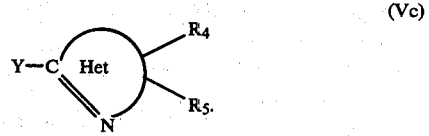

(Vc)

Compounds of the general formula I can also be prepared by a further process, by reacting guanidine derivatives of the general formula VI:

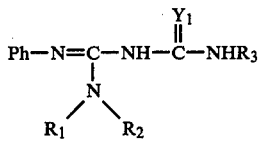 (VI)

or a tautomeric form thereof, in which Ph, $R_1$, $R_2$ and $R_3$ are as defined above and $Y_1$ is an oxo, thioxo or NH group, with a compound of the general formula VII:

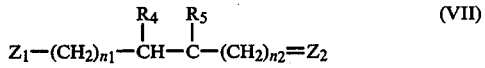 (VII)

in which $n_1$ oder $n_2$ are 0, 1, 2 or 3 with the proviso that $n_1$ and $n_2$ together are not more than 3, $Z_1$ is a halogen atom and $Z_2$ is an oxo group or the group consisting of hydrogen and halogen together, wherein the hydrogen atom can be part of a methylen group, or in case were $n_1$ or $n_2$ are both 0 $Z_1$ and $Z_2$ taken together make up the divalent alkylene radical

via an imino group to an aziridine derivative, in which $R_4$ and $R_5$ are hydrogen, and, if desired, carrying out additional process steps and/or, if desired, converting resulting compounds of the formula I into a salt, and/or, if desired, converting resulting salts of compounds of the formula I into free bases.

For example, a compound of the formula VI in which $Y_1$ is an oxo or thioxo group is reacted with a halogenoacetaldehyde of the formula VII, in which $Z_1$ is a halogen and $Z_2$ is an oxo group, preferably in a solvent and with or without the addition of an acid-binding agent.

Examples of solvents which can be used are lower alkanols, for example methanol, ethanol, isopropanol or butanol; ketones, for example acetone, butanone or methyl isopropyl ketone; ethers, for example 1,2-dimethoxyethane, diisopropyl ether, tetrahydrofuran or dioxan; carboxylic acid derivatives, for example acetonitrile, ethyl acetate or dimethylformamide; aromatic compounds, for example benzene, toluene or xylene, aliphatic or cycloaliphatic compounds, for example benzines and ligroins with boiling ranges between 60° C. and 180° C. and cyclohexane; and halogenated aliphatic hydrocarbons, for example methylene chloride, chloroform, carbon tetrachloride or 1,2-dichloroethane.

Examples of acid-binding agents which can be used are: inorganic bases, for example sodium bicarbonate, sodium carbonate, potassium carbonate, trisodium phosphate, sodium hydroxide or potassium hydroxide, or organic bases, for example triethylamine or benzyldimethylamine.

For the reaction of compounds of the formula VI with halogeno-acetaldehydes or compounds which split off halogenoacetaldehyde, for example corresponding acetals, preferably equimolar or approximately equimolar amounts of the two components are used. In particular, it can be appropriate to employ a slight excess (1-15 mol %) of the halogenoacetaldehyde or the compound which splits off halogenoacetaldehyde. For this purpose, the compound of the formula VI is dissolved or suspended in a solvent and the halogenoacetaldehyde or the compound which splits off halogenoacetaldehyde is added slowly. The acid-binding agent can likewise be introduced at the start or can be added only subsequently. The reaction is carried out at 0° C. to the boiling point of the solvent used, for example at a temperature of up to 150° C.; the preferred temperature range is from 20° C. to 100° C.

In an analogous manner, a compound of the formula VI in which Y is a thioxo group can also be reacted with a dihalogenoethane compound of the formula VII, in which $Z_1$ is a halogen atom and $Z_2$ is a halogen atom and a hydrogen atom, to give the same compounds of the formula I. In a manner analogous to that described above, the reactions are carried out in an organic solvent or in an excess of the dihalogenoethane compound of the formula VII which is used. Preferably, the reaction is carried out in a lower alkanol, for example methanol, ethanol, isopropanol or butanol.

The aziridines, which fall under the formula VII and in which $R_4$ and $R_5$ are hydrogen, can be reacted with a thiourea derivative of the formula VI in an aqueous-acid solution or preferably in a nonpolar solvent, for example in one of the abovementioned ketones, at a temperature between 0° C. and 100° C., but preferably between 0° C. and 30° C. However, if an aqueous-acid solution is used as the solvent, the reaction mixture must be rendered alkaline after the reaction has taken place, in order to obtain the resulting compound of the formula I in the form of the free base.

The compounds, according to the invention, of the formula I in which $R_1$ is as defined above and $R_2$ and/or $R_3$ are hydrogen can be converted by a further process, by reaction with an alkylating agent, such as an reactive ester of an aliphatic or cycloaliphatic alcohol to compounds of the formula I in which $R_2$ and/or $R_3$ have a meaning, other than hydrogen, which falls within the above definition for $R_2$ and $R_3$, after which, if desired, additional process steps are carried out and/or, if desired, resulting compounds of the formula I are converted to the free bases, and/or, if desired, converting resulting compounds of formula I into salts of compounds of formula I.

Reactive esters which can be used as alkylating agents are alkyl- or cycloalkyl halides, for example methyl- or cyclohexyliodide, lower alkyl fluorosulfonate, for example methyl fluorosulfonate, alkyl methanesulfonate, for example methyl methanesulfonate, alkyl toluenesulfonate, for example methyl toluenesulfonate, or a dialkyl sulfate, for example dimethyl sulfate.

The compounds, according to the invention, of the formula I in which $R_2$ and/or $R_3$ are hydrogen can be prepared by a further process, by detaching the amino protective group or groups from compounds of the general formula VIII:

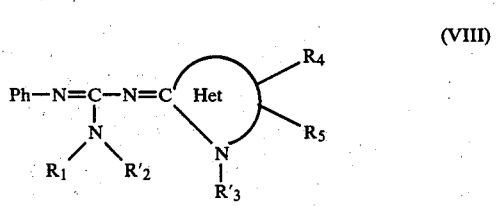 (VIII)

in which $R_1$, $R_4$, $R_5$, Ph and Het are as defined under formula I and one of the substituents $R_2'$ and $R_3'$ has the meaning defined for $R_2$ or $R_3$ and the other is an amino protective group, or both $R_2'$ and $R_3'$ are an amino protective group, and, if desired, carrying out additional process steps and/or, if desired, converting resulting compounds of the formula I into a salt and/or, if desired, converting resulting compounds of the formula I into free bases.

An amino protective group $R_2'$ and/or $R_3'$ is, in particular, an acyl group, such as acyl from an aliphatic, aromatic or araliphatic carboxylic acid, especially lower alkanoyl, for example acetyl or propionyl, or aroyl, for example benzoyl, or acyl from formic acid or from a carbonic acid half-derivative, for example a carbonic acid half-ester, such as formyl or lower alkoxycarbonyl, for example ethoxycarbonyl or tert.-butoxycarbonyl, or aryl-lower alkoxycarbonyl, for example benzyloxycarbonyl.

An acyl radical used as an amino protective group $R_2'$ and/or $R_3'$ is detached in a manner known per se, for example by solvolysis, in particular by means of alcoholysis, and also by means of hydrolysis. Detaching of an acyl radical $R_2'$ and/or $R_3'$ by alcoholysis can be carried out, for example, in the presence of a strongly basic agent, at elevated temperature, for example at about 50° C. to about 120° C. The alcohol used is in particular a lower alkanol, for example n-butanol or ethanol, and the strong base used is an alkali metal lower alkanolate, for example a sodium or potassium lower alkanolate, for example sodium n-butylate or ethylate or potassium n-butylate or ethylate or ethylate, or an alkali metal hydroxide, for example sodium hydroxide or potassium hydroxide.

Amino protective groups $R_2'$ and $R_3'$, for example lower alkoxycarbonyl groups, such as tert.-butoxycarbonyl, can be detached under particularly mild conditions by acidolysis, for example by treatment with trifluoroacetic acid.

A further amino protective group which can be detached under particularly mild conditions is an ethoxycarbonyl group which in the β-position carries a silyl group substituted by three hydrocarbon radicals, such as a triphenylsilyl, dimethyl-butyl-silyl or, in particular, trimethylsilyl group. With the amino group to be protected, a β-(tri-methylsilyl)-ethoxycarbonyl group of this type forms a corresponding β-tri-methylsilyl-ethoxycarbonylamino group, which can be detached under mild conditions by the action of fluoride ions. Reagents which donate fluoride ions are, for example, fluorides of quaternary organic bases, such as tetraethylammonium fluoride.

Attention must be paid to the fact that only those amino protective groups which are selectively detachable whilst retaining the structure of the compounds of the general formula I can be used as the amino protective group $R_2'$ and/or $R_3$.

The starting materials are known or, if they are novel, can be prepared by methods known per se. Where it seems appropriate, the starting materials used have already been described after the process described.

Compounds of the general formula IIa in which $X_2$ is a lower alkylthio group can be prepared, for example, from the corresponding thioureas of the general formula IX:

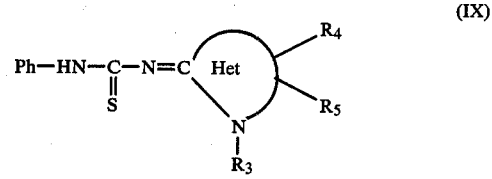

by reacting the latter with an alkylating agent of the formula $R_xZ_y$, in which $R_x$ is a lower alkyl group, for example a methyl or ethyl group, and $Z_y$ is, for example, a tosylate, lower alkyl sulfate, for example methylsulfate, lower alkane sulfonate, for example methanesulfonate, fluorosulfonate group or preferably a halide. These alkylating agents are embraced by the group of reactive esters of aliphatic or cycloaliphatic alcohols as listed above.

The reaction is carried out in one of the organic solvents already defined above. The solvent used is preferably an ether, for example diethyl ether, tetrahydrofuran or dioxan, a ketone, for example acetone or 2-butanone, a halogenated aliphatic hydrocarbon, for example chloroform or methylene chloride, or a lower alkanol, for example methanol or ethanol. An alkyl halide in methanol or ethanol is particularly suitable. In general, the alkylating agent is used in at least equimolar amount. The alkylation can, as appropriate, be carried out at room temperature or at higher temperatures and if necessary in a closed reaction vessel.

Compounds of the general formula IX, in turn, can be prepared from the imino compounds of the formula III:

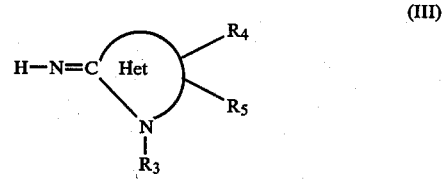

which have already been mentioned and are known, by reaction with a substituted or unsubstituted phenyl isothiocyanate of the formula Ph-NCS, in approximately equimolar amounts in one of the inert organic solvents already defined above, preferably in benzene, methylene chloride or chloroform, at temperatures of 0° C. to room temperature for 2-24 hours.

Compounds of the formula IIb in which $X_3$, as a detachable group, is halogen, preferably chlorine, are obtained by the method described by E. Kühle, Angew. Chem., Intern. Ed., volume 8 (1969), page 24–26, by reacting an isocyanide dihalide of the formula X:

with an amine of the formula $HNR_1R_2$ in the presence of a trialkylamine, for example triethylamine, in an inert, aprotic, anhydrous solvent. Compounds of the formula X can also be in the form of immonium chlorides. The solvent used is, for example, an ether for example diethyl ether, dioxan or tetrahydrofuran, a halogenated aliphatic hydrocarbon, for example chloroform or methylene chloride, or an aromatic hydrocarbon, for example benzene, toluene or xylene. Compounds of the general formula X are known and can be prepared in a manner analogous to that described in Angew. Chem., Intern. Ed. volume 6 (1967), page 649.

Compounds of the general formula IIb in which the detachable group $X_3$ is halogen can be converted easily in a known manner to compounds of the formula IIb in which $X_3$ is a lower alkoxy group.

Starting compounds of the general formula IIc in which $X_1$, as a detachable group, is a halogen, preferably chlorine, can be prepared by reacting an immonium chloride of the formula:

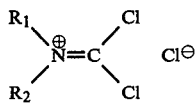

with an imino compound of the formula III:

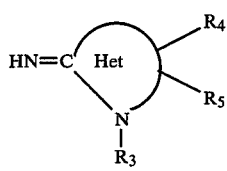

in accordance with the method described by R. G. Glushkow, Khim.-Farmatsevt. Zh.12, No. 6, 59-64/1978.

The reaction is carried out in a manner analogous to that described above for the reaction of a compound of the formula X.

Starting compounds of the general formula VI in which $Y_1$ is, for example, an oxo or thioxo group and $R_3$ differs from hydrogen can be prepared by reacting a guanidine compound of the formula XI:

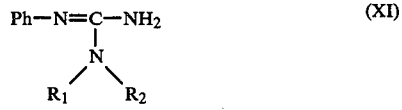
(XI)

with a lower alkyl isothiocyanate or lower alkyl isocyanate. The reaction is carried out in an organic solvent, preferably in an ether, for example diethyl ether, diisopropyl ether, tetrahydrofuran or dioxan, or a carboxylic acid derivative, for example acetonitrile, at a temperature which is between 0° C. and the boiling point of the solvent, preferably at 20° C. to 100° C.

Compounds of the general formula VI in which, for example, $Y_1$ is a thioxo group and $R_3$ is hydrogen can be prepared by the process described by H. Hartmann et al., J. Prakt. Chem. 315 (1973), page 144. Guanidine compounds of the general formula XI are reacted with a lower alkoxycarbonyl isothiocyanate to give a compound of the formula XII:

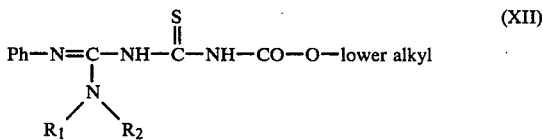
(XII)

which is converted to a compound of the formula VI by hydrolysis with a mineral acid, preferably hydrochloric acid.

Compounds of the general formula VIII can be prepared by one of the processes (1)-(3) described above for the preparation of compounds of the general formula I, but $R_2$ and/or $R_3$ in the starting materials used are an acyl radical. These acyl radicals used as amino protective groups are as defined above.

The processes described can be carried out in the usual manner at room temperature, with cooling or warming, under normal pressure or elevated pressure and, if necessary, in the presence or absence of a diluent, catalyst or condensing agent. If necessary, the reactions can also be carried out in the atmosphere of an inert gas, for example nitrogen.

In resulting compounds, substituents can be introduced, modified or detached within the scope of the definition of the end products. Starting compounds and processes for their production are also part of the invention if they are new.

Depending on the process conditions and starting materials, the end products are obtained in the free form or in the form of their salts, especially acid addition salts, which is also included in the invention. The acid addition salts of the novel compounds can be converted to the free compound in a manner known per se, for example using basic agents, such as alkalis or ion exchange resins. On the other hand, the resulting free bases can form salts with organic or inorganic acids. The acids used to prepare acid addition salts are in particular those which are suitable for forming therapeutically usable salts. Examples of such acids are: hydrogen halide acids, sulfuric acids, phosphoric acids, nitric acid, perchloric acid, aliphatic, alicyclic, aromatic or heterocyclic carboxylic or sulfonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicylic acid or p-aminosalicyclic acid, embonic acid, methanesulfonic acid, ethanesulfonic acid, hydroxyethanesulfonic acid or ethylenesulfonic acid; a halogenobenzenesulfonic acid or toluenesulfonic acid, naphthalenesulfonic acid or sulfanilic acid; methionine, tryptophan, lysine or arginine.

These or other salts of the novel compounds, for example the picrates, can also be used to purify the resulting free bases, by converting the free bases to salts, separating these off an liverating the bases from the salts again. Because of the close relationship between the novel compounds in the free form and in the form of their salts, what is stated in this specification in respect of the free compounds also applies by analogy to the corresponding salts.

The invention also relates to those embodiments of a process in which a process is discontinued at any stage or in which a compound obtainable as an intermediate at any stage is used as the starting material is formed under the reaction conditions or, if desired, is used in the form of a salt. The novel intermediates resulting therefrom are also included in the invention.

The invention also includes therapeutic compositions of matter which consist of an antihyperglycaemically effective amount of the compounds of the general formula I, or of an acid addition salt, and a pharmacologically acceptable solid carrier or liquid diluents.

The pharmaceutical preparations according to the invention contain at least one compound of the general formula I, or a salt thereof, as the active ingredient, together with a conventional pharmaceutical carrier. The nature of the carriers substantially depends on the field of application. The pharmaceutical compositions of matter according to the invention, which contain compounds of the formula I as active ingredients, can be administered orally, parenterally or rectally.

Preparations used for the oral treatment of hyperglycaemia are, in particular, solid dosage unit forms, such as tablets, sugar-coated tablets and capsules, which preferably contain between 10 and 90% of an active ingredient of the general formula I or of a salt, to enable daily doses of between 1.5 and 100 mg/kg to be administered to warm-blooded animals. To prepare tablets and sugar-coated tablet cores, the compounds of the general formula I are combined with solid, pulverulent carriers, such as lactose, sucrose, sorbitol, maize starch, potato starch or amylopectin, cellulose derivatives or gelatine, preferably with the addition of lubricants, such as magnesium stearate or calcium stearate, or polyethylene glycols of suitable molecular weight. Sugar-coated tablet cores are then coated, for example with concentrated sugar solutions, which can also contain, for example, gum arabic, talc and/or titanium dioxide, or with a lacquer dissolved in readily volatile organic solvents or solvent mixtures. Colorants can be added to these coatings, for example to distinguish different dosages of active ingredient. Soft gelatine capsules and other sealed capsules consist, for example, of a mixture of gelatine and glycerol and can contain, for example, mixtures of a compound of the formula I with polyethylene glycol. Dry-filled capsules contain, for example, granules of an active ingredient with solid, pulverulent carriers, for example lactose, sucrose, sorbitol or mannitol; starches, such as potato starch, maize starch or amylopectin, cellulose derivatives and gelatine, as well as magnesium stearate or stearic acid.

Suitable dosage unit forms for rectal administration are, for example, suppositories, which consist of a combination of an active ingredient with a suppository base based on natural or synthetic triglycerides (for example cacao butter), polyethylene glycols or suitable higher fatty alcohols, and gelatine rectal capsules, which contain a combination of the active ingredient and polyethylene glycols.

Ampoule solutions for parenteral, and in particular intramuscular or intravenous, administration contain a compound of the formula I or a salt thereof in a concentration of preferably 0.5 to 5% in the form of an aqueous dispersion prepared with the aid of conventional solubilising agents and/or emulsifiers and, if appropriate, stabilisers, or preferably an aqueous solution of a pharmaceutically acceptable, water-soluble acid addition salt of a compound of the general formula I.

For liquids which are to be taken orally, such as syrups and elixirs, the concentration of the active ingredient is so chosen that an individual dose can be measured out easily, for example as a teaspoonful or as the contents of a measuring spoon, for a example a 5 ml measuring spoon, or as a multiple of these volumes.

The following examples (a) to (e) are intended to illustrate the preparation of some typical administration forms, but in no way represents the only embodiments of these.

(a) 250.0 g of active ingredient are mixed with 550.0 g of lactose and 292.0 of potato starch and the mixture is moistened with an alcoholic solution of 8 g of gelatine and granulated through a sieve. After drying, 60.0 g of talc, 10.0 g of magnesium stearate and 20.0 g of colloidal silica are mixed in and the mixture is compressed to 10,000 tablets, each weighing 125 mg and containing 25 mg of active ingredient; if desired, the tablets can be provided with breaking notches for finer adjustment of the dosage.

(b) Granules are prepared from 100.0 g of active ingredient, 379.0 g. of lactose and an alcoholic solution of 6.0 g of gelatine and, after drying, these granules are mixed with 10.0 g of colloidal silica, 40.0 g of talc, 60.0 g of potato starch and 5.0 g of magnesium stearate and the mixture is compressed to 10,000 sugar-coated tablet cores. These are then coated with a concentrated syrup of 533.5 g of crystalline sucrose, 20.0 g of Shellack, 75.0 g of gum arabic, 250.0 g of talc, 20.0 g of colloidal silica and 15. g of colorant and dried. The resulting sugar-coated tablets each weigh 150 mg and each contain 10 mg of active ingredient.

(c) 25.0 g of active ingredient and 1.975 g of finely ground suppository base (for example cacao butter) are mixed thoroughly and then melted. 1,000 2.0 g suppositories are cast from the melt, which is kept homogeneous by stirring. Each suppository contains 25 mg of active ingredient.

(d) To prepare a syrup containing 0.25% of active ingredient, 1.5 liters of glycerol, 42 g of methyl p-hydroxybenzoate, 18 g of n-propyl p-hydroxybenzoate and with slight warming, 25.0 g of active ingredient are dissolved in 3 liters of distilled water and 4 liters of 70% sorbitol solution, 1,000 g of crystalline sucrose, 350 g of glucose and an aroma substance, for example 250 g of "Orange Peel Soluble Fluid" form Eli Lilly and Co., Indianapolis or 5 g of natural lemon aroma and 5 g of "Halb and Halb" ("half and half") essence, both from Haarmann and Reimer, Holzminden, Germany, are added, the resulting solution is filtered and the filtrate is made up to 10 liters with distilled water.

(e) To prepare a drop solution containing 1.5% of active ingredient and 30 g of sodium cyclamate are dissolved in a mixture of 4 liters of ethanol (96%) of 1 liter of propylene glycol. On the other hand, 3.5 liters of 70% sorbitol solution are mixed with 1 liter of water and the mixture is added to the above solution of the active ingredient. An aroma substance, for example 5 g of cough sweet aroma or 30 g of grapefruit essence, both from Haarmann and Reimer, Holzminden, Germany, is then added and the whole is mixed well and filtered and the filtrate is made up to 10 liters with distilled water.

The following examples illustrate the preparation of the novel compounds of the general formula I, but do not in any way limit the scope of the invention. The temperatures are in degrees Centigrade.

EXAMPLE 1

21.25 g (021. mol) of triethylamine are added dropwise to a solution, cooled to 5°, of 24.2 g (0.1 mol) of 2,5-dimethyl-3-isoxazolidine-imine hydroiodide [cf. Bull. Soc. Chim. Fr. 1974, 1651–1655] in 120 ml of acetonitrile, with stirring. Whilst continuing to cool, 22.47 g (0.1 mol) of N-phenyl-4-morpholinecarboximidoyl chloride [cf. Chem. Ber. 105, 1532–1539 (1972)] are added in portions, the reaction temperature being kept at 5°–10°. After the addition is complete, the reaction mixture is stirred for a further ½ hour at 10° and for one hour at room temperature. The reaction mixture is filtered, the filter residue is washed with a little acetonitrile and the filtrate is evaporated in vacuo. Ice-cold 2 N sodium hydroxide solution is added to the residue and the mixture is extracted several times with chloroform. The combined chloroform phases, which have been washed with water until neutral, are evaporated after drying over sodium sulfate and crude N-(2,5-dimethyl-3-isoxazolidin-ylidene)-N'-phenyl-4-morpholinecarboximide-amide is obtained. The fumarate prepared by reaction with fumaric acid melts at 192°–193° after recrystallisation from ethanol/ethyl acetate.

EXAMPLE 2

Crude N-(2,5-dimethyl-3-isoxazolidinylidene)-N'-phenyl-1-piperidinecarboximide-amide is obtained analogously to Example 1, using 12.1 g (0.05 mol) of 2,5-dimethyl-3-isoxazolidine-imine-hydroiodide and 11,13 (0.05 mol) of N-phenyl-1-piperidine-carboximidoyl chloride [cf. Organometal. Chem. Synt. 1, 23–30 (1970–71)], 10.63 g (0.105 mol) of triethylamine and 60 ml of acetonitrile as the starting materials. The fumarate prepared from this product with fumaric acid melts at 171.5°–173° after recrystallisation from isopropanol/ethyl acetate.

EXAMPLE 3

Crude N-(2-methyl-3-isoxazolidinylidene)-2'-phenyl-4-morpholinecarboximide-amide [melting point 80°–88°, from petroleum ether] is obtained analogously to Example 1, using 11.4 g (0.05 mol) of 2-methyl-3-isoxazolidine-imine hydroiodide [cf. Bull. Soc. Chim. Fr. 1974, 1651–1655], 11.23 g (0.05 mol) of N-phenyl-4-morpholinecarboximidoyl chloride, 10.63 g (0.105 mol) of triethylamine and 60 ml of acetonitrile as the starting materials. The fumarate prepared from this product with fumaric acid melts at 167°–168° after recrystallisation from ethanol/ether.

EXAMPLE 4

Crude N-(2,5,5-trimethyl-3-isoxazolidinylidene)-N'-phenyl-4-morpholinecarboximide-amide is obtained analogously to Example 1, using 12.8 g (0.05 mol) of 2,5,5-trimethyl-3-isoxazolidine-imine hydroiodide (cf. Bull. Soc. Chim. Fr. 1973, 1651–1655), 11.23 g (0.05 mol) of N-phenyl-4-morpholine-carboximidoyl chloride, 10.63 g (0.105 mol) of triethylamine and 60 ml of acetonitrile as the starting materials. The fumarate prepared from this product with fumaric acid melts at 203°–204° after recrystallisation from ethanol/ether.

EXAMPLE 5

15.18 g (0.15 mol) of triethylamine are added dropwise to a solution of 12.26 g (0.05 mol) of N,N-tetramethylene-N'-phenylchloroformamidinium chloride (or phenylimino-chlorocarbonic acid pyrrolidinylamide hydrochloride) [cf. Chem. Ber. 97, 1232–1245 (1964)] and 12.1. g (0.05 mol) of 2,5 dimethyl-2-isoxazolidine-imine hydroiodide in 50 ml of acetonitrile, with stirring and cooling, the reaction temperature being kept at 5°–10°. The reaction mixture is stirred at room temperature for a further 15 hours and is then filtered. The filtrate is evaporated in vacuo and the residue is filtered with chloroform through silica gel with a particle size of 0.063–0.200 mm. The fractions containing the desired product are combined and washed with ice-cold sodium hydroxide solution and water. The chloroform phase is dried over sodium sulfate and evaporated in vacuo and crude N-(2,5-dimethyl-3-isoxazolidinylidene)-N'-phenyl-1-pyrrolidinecarboximide-amide is obtained. The maleate prepared from this product with maleic acid melts at 114°–116° after recrystallisation from acetate/isopropanol.

EXAMPLE 6

(a) 19.5 g (0.05 mol) of N-(1,3-dimethyl-2-imidazolidinylidene)-N'-phenyl-carbamimido-thiomethylester hydroiodide and 10.66 g (0.15 mol) of pyrrolidine are added to 200 ml of isopropanol, with stirring. The reaction mixture is refluxed for 36 hours and then evaporated. The residue is partitioned between chloroform and 1 N sodium hydroxide solution. The organic phase, which is washed with water and dried over sodium sulfate, is evaporated and the residue is filtered with a 40:10:1 mixture of chloroform/methanol/concentrated ammonia through silica gel with a particle size of 0.063.0.200 mm. The fractions containing the desired product are evaporated in vacuo. The crude N-(1,3-dimethyl-2-imidazolidinylidene)-N'-phenyl-1-pyrrolidinecarboximide-amide which is thus obtained is converted with maleic acid to the maleate, which melts at 126°–127° after recrystallisation from ethyl acetate/isopropanol.

The starting compound, N-(1,3-dimethyl-2-imidazolidinylidene)-N'-phenylcarbamimido-thiomethyl ester hydroiodide, is prepared as follows:

(b) A solution of 52.9 of cyanogen bromide in 300 ml of toluene is added dropwise in the course of 1 hour to a solution of 44.1 g (0.5 mol) of N,N'-dimethylethylenediamine in 300 ml of toluene, with stirring. The reaction mixture is stirred for a further two hours at 80°. The mixture is allowed to cool to room temperature and is filtered and the residue is washed with ether. The crude 1,3-dimethyl-2-imino-imidazolidine hydrobromide obtained after drying in vacuo melts at 153°–160°.

(c) 30.4 g (0.3 mol) of triethylamine are added to a suspension of 58.2 g (0.3 mol) of 1,3-dimethyl-2-imino-imidazolidine hydrobromide in 470 ml of chloroform, at 5°, with stirring. A solution of 40.6 g (0.3 mol) of phenyl isothiocyanate in 235 ml of chloroform is then added dropwise and the reaction mixture is refluxed for 15 hours. After cooling, it is washed with water, dried over sodium sulfate and evaporated in vacuo. Crude N-(1,3-dimethyl-2-imidazolidinylidene)-N'-phenyl-thiourea is obtained and after recrystallisation from ethanol this melts at 195°–196°.

(d) A solution of 21.3 g (0.15 mol) of methyl iodide in 35 ml of tetrahydrofuran is added dropwise to a suspension of 24.8 g (0.1 mol) of N-1,3-dimethyl-2-imidazolidinylidene)-N'-phenyl-thiourea in 165 ml of tetrahydrofuran, at room temperature, with stirring. The reaction mixture is stirred at room temperature for 15 hours and 160 ml of ether are then added. The precipitate is filtered off, washed with ether and dried in vacuo. The resulting N-(1,3-dimethyl-2-imidazolidinylidene)-N'-phenylcarbamimido-thiomethyl ester hydroiodide melts at 157°–158°.

EXAMPLE 7

(a) A solution of 19.6 g of N-[3-methyl-4-(1,3,4)-thiadiazolin-2-ylidene]-N'-phenylcarbamimido-thiomethyl ester hydroiodide and 10.7. g of pyrrolidine in 150 ml of isopropanol is refluxed for 15 hours. The reaction mixture is then evaporated to dryness and the residue is chromatographed through a short column packed with silica gel. First chloroform and then a chloroform/acetone mixture (95:5) are used as the eluants. The final fractions are combined and stirred with ether and the hydroiodide thus obtained is converted to the hydrochloride with the aid of an ion exchange resin. The resulting N-[3-methyl-4-(1,3,4)-thiadiazolin-2-ylidene]-N'-phenyl-1-pyrrolidine-carboximideamide hydrochloride melts at 217°–218° (decomposition).

The N-[3-methyl-4-(1,3,4)-thiadiazolin-2-ylidene]-N'-phenylcarbamimido-thiomethyl ester hydroiodide used as the starting compound is obtained as follows:

(b) A suspension of 52.7 g of 2-imino-3-methyl-4-(1,3,4)-thiadiazoline hydroiodide and 24.3 g of potassium tert.-butylate in 500 ml of tetrahydrofuran is stirred at room temperature for 1 hour. It is then filtered through a bed of diatomaceous earth. 29.3 g of phenyl isothiocyanate are added dropwise in the course of 5 minutes to the filtrate and the mixture is stirred for 16 hours at room temperature. The reaction mixture is then evaporated to dryness and the residue is stirred with ether, filtered off with suction and again stirred with hot isopropanol. N-[3-Methyl-4-(1,3,4)-thiadiazolin-2-ylidene]-N'-phenylthiourea with a melting point of 174°–175° is thus obtained.

(c) 43.4 g of methyl iodide are added to a solution of 25.5 g of the compound obtained in (b) in 300 ml of acetonitrile. The solution is refluxed for 30 minutes. The crystals which have separated out on cooling are filtered off with suction, washed, first with acetonitrile and then with ether, and dried. N-[3-Methyl-4(1,3,4)-thiadiazolin-2-ylidene]-N'-phenyl-carbamimido-thiomethyl-ester hydroiodide with a melting point of 190° (decomposition) is thus obtained.

EXAMPLE 8

(a) 64.1 g of methyl iodide are added to a solution of 17.6 g of 2-amino-5-methyl-1,3,4-thiadiazole in 350 ml isopropanol. The solution is refluxed for 15 hours. The reaction mixture is then evaporated to dryness, the crystalline evaporation residue is stirred with ethyl acetate and the solvent is filtered off with suction. The crystalline residue is washed, first with ethyl acetate and then with ether, and then dried. 2-Imino-3,5-dimethyl-4-(1,3,4)-thiadiazoline hydroiodide with a melting point of 208° (decomposition) is thus obtained.

The following salts of the 2-imino compounds can be prepared analogously:
(b) 2-imino-3-methyl-5-ethyl-4-(1,3,4)-thiadiazoline hydroiodide, melting point 137°–138° (decomposition)
(c) 2-imino-3-methyl-5-trifluoromethyl-4-(1,3,4)-thiadiazoline hydroiodide, melting point 187°–188° (decomposition)
(d) 2-imino-3-methyl-5-methylmercapto-4-(1,3,4)-thiadiazoline hydroiodide, melting point 205°–206°
(e) 2-imino-3-methyl-4-phenyl-4-thiazoline hydroiodide, melting point 235° (decomposition)
(f) 2-imino-3,5-dimethyl-4-thiazoline hydroiodide, melting point 187°–188°
(g) 2-imino-1,3-dimethyl-4-imidazoline hydroiodide, melting point 126°–127°
(h) 2-imino-3-methyl-4-oxazoline hydroiodide, melting point 191°–192° (decomposition)
(i) 2-imino-3,4,5-trimethyl-4-oxazoline hydroiodide, melting point 169°–171° and
(j) 2-imino-3,5-dimethyl-4-(1,3,4)-oxadiazoline hydroiodide, melting point 169° (decomposition).

EXAMPLE 9

In accordance with the procedure of Example 7(b), but using an equivalent amount of the 2-imino compound obtained in Example 8, the following thioureas are obtained on reaction with an equivalent amount of phenyl isothiocyanate:
(a) N-[3,5-dimethyl-4-(1,3,4)-thiadiazolin-2-ylidene]-N'-phenylthiourea, melting point 175°–176°
(b) N-[3-methyl-5-ethyl-4-(1,3,4)-thiadiazolin-2-ylidene]-N'-phenylthiourea, melting point 135°–136°
(c) N-[3-methyl-5-methylmercapto-4-(1,3,4)-thiadiazolin-2-ylidene]-N'-phenylthiourea, melting point 160°–161°
(d) N-(3-methyl-4-thiazolin-2-ylidene)-N'-phenyl-thiourea, melting point 174°–175°
(e) N-(3-methyl-4-phenyl-4-thiazolin-2-ylidene)-N'-phenylthiourea, melting point 183°–184°
(f) N-(3,5-dimethyl-4-thiazolin-2-ylidene)-N'-phenylthiourea, melting point 185°–186°
(g) N-(1,3-dimethyl-4-imidazolin-2-ylidene)-N'-phenyl-thiourea, melting point 221°–222°
(h) N-(3-methyl-4-oxazolin-2-ylidene)-N'-phenyl-thiourea, melting point 169°–170° and
(i) N-(3,4,5-trimethyl-4-oxazolin-2-ylidene)-N'-phenyl-thiourea, melting point 192°–192.5°.

The following compounds are prepared analogously:
(j) N-(3-allyl-4-thiazolin-2-ylidene)-N'-phenylthiourea with a melting point of 129.5°–130.5°, from 2-imino-3-allyl-4-thiazoline hydroiodide and phenyl isocyanate, and
(k) N-(3-methyl-thioazolidin-2-ylidene)-N'-phenylthiourea with a melting point of 170°–172°, from 2-imino-3-methyl-thiazolidine hydroiodide and phenyl isocyanate.

EXAMPLE 10

The phenyl ester hydroiodides are obtained by the procedure according to Example 7(c), but using the thioureas listed above in Example 9, in each case in specific solvents:
(a) in isopropanol, N-[3,5-dimethyl-4(1,3,4)-thiadiazolin-2-ylidene]-N'-phenylcarbamimido-thiomethyl ester hydroiodide, melting point 134°–135.5°;
(b) in tetrahydrofuran, N-[3-methyl-5-ethyl-4-(1,3,4)-thiadiazolin-2-ylidene]-N'-phenylcarbamimido-thiomethyl ester hydroiodide, red oil;
(c) in tetrahydrofuran, N-[3-methyl-5-methylmercapto-4-(1,3,4)-thiadiazolin-2-ylidene]-N'-phenylcarbamimido-thiomethyl ester hydroiodide, melting point 160°–161°;
(d) in tetrahydrofuran, N-(3-methyl-4-thiazolin-2-ylidene)-N'-phenylcarbamimido-thiomethyl ester hydroiodide melting point 174°–175°;
(e) in tetrahydrofuran, N-(3-methyl-4-phenyl-4-thiazolin-2-ylidene)-N'-phenylcarbamimido-thiomethyl ester hydroiodide, melting point 183°–184°;
(f) in tetrahydrofuran, N-(3,5-dimethyl-4-thiazolin-2-ylidene)-N'-phenylcarbamimido-thiomethyl ester hydroiodide, melting point 185°–186°;
(g) in acetonitrile, N-(1,3-dimethyl-4-imidazolin-2-ylidene)-N'-Phenylcarbamimido-thiomethyl ester hydroiodide, melting point 221°–222°;
(h) in isopropanol, N-(3-methyl-4-oxazolin-2-ylidene)-N'-phenylcarbamimido-thiomethyl ester hydroiodide, melting point 140°–141°;
(i) in isopropanol, N-(3,4,5-trimethyl-4-oxazolin-2-ylidene)-N'-phenylcarbamimido-thiomethyl ester hydroiodide, melting point 192°–192.5°
(j) in isopropanol, N-(3-allyl-4-thiazolin-2-ylidene)-N'-phenylcarbamimido-thiomethyl ester hydroiodide, melting point 138°–139°; and (k) in tetrahydrofuran, N-(3,4,5-trimethyl-4-oxazolin-2-ylidene)-N'-phenylcarbamimido-thiomethyl ester hydroiodide, melting point 139°–141°.

EXAMPLE 11

In accordance with the procedure of Example 7(a), the corresponding methylthio-hydroiodides of Example 10 and the corresponding amines of the general formula $HNR_1R_2$ are reacted in a molar ratio 1:3 in isopropanol, tert.-butanol or ethanol, which is boiling under reflux, to give the compounds a-k listed below, in the form of the hydroiodides. The hydroiodides are isolated as such and converted to the hydrochlorides with the aid of an anion exchange resin or, if desired, converted to the free bases with aqueous alkali. Other salts can also be prepared by reacting the free bases with a suitable acid.

(a) N-[3,5-dimethyl-4-(1,3,4)-thiadiazolin-2-ylidene]-N'-phenyl-1-pyrrolidine-carboximide-amide as the free base, melting point 98°–99°;

(b) N-[3-methyl-5-ethyl-4-(1,3,4)-thiadiazolin-2-ylidene]-N'-phenyl-1-pyrrolidine-carboximide-amide as the free base, melting point 85°–86°;

(c) N-[3-methyl-5-methylmercapto-4-(1,3,4)-thiadiazolin-2-ylidene]-N'-phenyl-1-pyrrolidine-carboximideamide as the free base, melting point 98°–99°;

(d) N-(3-methyl-4-thiazolin-2-ylidene)-N'-phenyl-1-pyrrolidinecarboximide-amide as the free base, melting point 129°–130°;

(e) N-(3-Methyl-4-phenyl-4-thiazolin-2-ylidene)-N'-phenyl-1-pyrrolidine-carboximide-amide as the hydrochloride-melting point 196°–197°;

(f) N-(3,5-dimethyl-4-thiazolin-2-ylidene)-N'-phenyl-1-pyrrolidine-carboximide-amide as the hydrochloride, melting point 220.5°–221.5°;

(g) N-(1,3-dimethyl-4-imidazolin-2-ylidene)-N'-phenyl-1-pyrrolidine-carboximide-amide, 2HCl, melting point 170° (decomposition);

(h) N-(3-methyl-4-oxazolin-2-ylidene)-N'-phenyl-1-pyrrolidinecarboximide-amide as the free base, melting point 94.5°–95.5°;

(i) N-(3,4,5-trimethyl-4-oxazolin-2-ylidene)-N'-phenyl-1-pyrrolidine-carboximide-amine as the hydrochloride, melting point 161°–163°;

(j) N-(3-allyl-4-thiazolin-2-ylidene)-N'-phenyl-1-pyrrolidinecarboximide-amide as the free base, melting point 91°–92°;

(k) N-(3,4,5-trimethyl-4-oxazolin-2-ylidene)-N'-phenyl-1-pyrrolidine-carboximide-amide as the hydrochloride, melting point 225°–226°;

(l) N-[3,5-dimethyl-4-(1,3,5)-thiadiazolin-2-ylidene]-N'-phenyldimethylamino-carboximide-amide as the hydrochloride, melting point 238°–239.5° (decomposition); and (m) N-(3,4,5-trimethyl-4-oxazolin-2-ylidene)-N'-phenyldimethylamino-carboximide-amide as the free base, melting point 84°–86°.

EXAMPLE 12

A solution of 9.3 g of 2-imino-3-methyl-thiazolidine and 10.3 g of N-ethyldiisopropylamine in 50 ml of acetonitrile is added dropwise in the course of 15 minutes, at room temperature, to a solution of 14.8 g of N-phenyl-4-morpholine-carboximidoyl chloride in 50 ml of acetonitrile. The reaction mixture is then stirred for 2 hours at room temperature and then for a further 3 hours under reflux. The reaction mixture is evaporated to dryness, the crystalline residue is stirred with isopropanol, the solvent is filtered off with suction and the resulting solid product is then stirred with 50 ml of water for 30 minutes, filtered off with suction, washed, first with water and then with isopropanol, and dried. The N-(3-methyl-thiazolidin-2-ylidene)-N'-phenyl-4-morpholine-carboximide-amide thus obtained melts at 144.5°–145.5°.

EXAMPLE 13

The base is liberated from 18.5 g of 2-imino-3-methyl-5-trifluoromethyl-4-(1,3,4)-thiadiazoline hydroiodide with 10% sodium hydroxide solution and is taken up in methylene chloride and the solution is dried over anhydrous magnesium sulfate and evaporated. The base thus obtained and 7.6 of N-ethyldiisopropylamine are dissolved in 50 ml of acetonitrile and this solution is added dropwise in the course of 15 minutes to a solution of 11.9 g of N-phenyl-4-morpholinecarboximidoyl chloride in 50 ml of acetonitrile. The reaction mixture is then stirred for 4 hours at room temperature and then evaporated to dryness, the residue is stirred with ether, the mixture is filtered with suction, the ether extract is evaporated and the evaporation residue is chromatographed on a short column packed with silica gel. First methylene chloride and then a 97:3 mixture of methylene chloride and acetone are used as the eluants. The middle fractions are combined, stirring with a little hexane, filtered off with suction, washed with hexane and dried. The N-[3-methyl-5-trifluoromethyl-4-(1,3,4)-thiadiazolin-2-ylidene]-N'-phenyl-4-morpholine-carboximide-amide thus obtained melts at 110.5°–112°.

EXAMPLE 14

The base is liberated from 14.6 g of 2-imino-3-methyl-4-(1,3,4)-thiadiazoline hydroiodide with 30% sodium hydroxide solution and taken up in methylene chloride and the solution is dried over anhydrous magnesium sulfate and evaporated. The base thus obtained and 7.1 g of N-ethyldiisopropylamine are dissolved in 50 ml of acetonitrile and this solution is added dropwise in the course of 15 minutes to a solution of 11.2 g of N-phenyl-4-morpholine-carboximidoyl chloride in 50 ml of acetonitrile. The mixture is then stirred for 1 hour at room temperature and then for a further 3 hours under reflux. The reaction mixture is evaporated to dryness and the evaporation residue is chromatographed on a column packed with silica gel. Chloroform is used as the eluant. The base thus obtained is converted to the hydrochloride with alcoholic hydrochloric acid. After recrystallisation from acetonitrile/ethyl acetate, pure N-[3-methyl-4-(1,3,4)-thiadiazolin-2-ylidene]-N'-phenyl-4-morpholine-carboximide-amide hydrochloride with a melting point of 201.5°–202.5° is obtained.

EXAMPLE 15

Following the procedure described in Example 14, N-[3-methyl-4-(1,3,4)-thiadiazolin-2-ylidene]-N'-phenyl-1-piperidine-carboximide-amide with a melting point of 94.5°–95.5° is obtained from 8.6 g of 2-imino-3-methyl-4-(1,3,4)-thiadiazoline and 16.7 g of N-phenyl-1-piperidine-carboximidoyl chloride.

EXAMPLE 16

Following the procedure described in Example 14, N-(3-methyl-4-thiazolin-2-ylidene)-N'-phenyl-4-morpholine-carboximide-amide hydrochloride with a melting point of 209°–210° is obtained from 6.3 g of 2-imino-3-methyl-4-thiazoline and 11.2 g of N-phenyl-4-morpholine-carboximidoyl chloride.

EXAMPLE 17

12.0 g of 2-imino-3,5-dimethyl-4-(1,3,4)-oxadiazoline hydroiodide are reacted in the manner described in Example 8 with 11.2 g of N-phenyl-4-morpholine-carboximidoyl chloride. However, the reaction mixture is stirred only at room temperature and specifically is stirred for 16 hours. The reaction mixture is evaporated and chromatographed on a column packed with silica gel. First chloroform, then a 95:5 mixture of chloroform and acetone and finally 95:5 chloroform/methanol are used as the eluants. A hydrochloride is obtained from the final fraction and this is stirred with 30% sodium hydroxide solution. The base, which at first is oily, soon crystallises. The N-[3,5-dimethyl-4(1,3,4)-oxadiazolin-2-ylidene]-N'-phenyl-4-morpholine-carboximide-amide thus obtained melts at 117°-118°.

EXAMPLE 18

43.3 g (0.21 mol) of N-phenyl-N', N'-tetramethylene-thiourea [see J. Org. Chem. 23, 1760–1764 (1958)] are added, with stirring, to 200 ml of tetrahydrofuran and 111 ml of a 20% solution of phosgene in toluene (0.21 mole), care being taken to ensure that the temperature does not exceed 35°. Stirring is continued at 20° for a further 15 minutes; the temperature is then lowered to 10°, and 100 ml of acetonitrile and 50.8 g (0.21 mol) of 2,5-dimethyl-3-isoxazolidine-imine-hydroiodide are added to the reaction mixture (suspension of N,N-tetramethylene-N'-phenyl-chloroformamidinium chloride). After the dropwise addition of 64.8 g (0.64 mol) of triethylamine at 10°-15°, the suspension is stirred for a further 12 hours at 20°. It is subsequently filtered; the filtrate is concentrated in vacuo, and the residue is dissolved in ice-cold 2 N hydrochloric acid. The crude N-(2,5-dimethyl-3-isoxazolidinylidene)-N'-phenyl-1-pyrrolidinecarboximide-amide-hydrochloride is extracted with chloroform, and the chloroform extract is washed with 2 N sodium hydroxide solution and water; it is then dried over sodium sulfate and concentrated by evaporation to thus obtain crude N-(2,5-dimethyl-3-isoxazolidinylidene)-N'-phenyl-1-pyrrolidinecarboximide-amide.

The maleate produced therefrom with maleic acid melts at 114°-116° (from ethyl acetate).

Varient

A further simplification of the process comprises adding dropwise phenylisothiocyanate to a solution of pyrrolidine in ether or tetrahydrofuran; introducing into the formed suspension of N-phenyl-N', N'-tetramethylene-thiourea an equivalent amount of phosgene; and subsequently treating the reaction mixture in the manner described above.

EXAMPLE 19

A mixture of 3.6 g (0.05 mol) of pyrrolidine and 15.2 g (0.45 mol) of triethylamine is added dropwise at −10° to 0°, with stirring, to a solution of 8.7 g (0.05 mol) of phenylisocyanide dichloride in 120 ml of acetonitrile. The reaction mixture is stirred at 0° for a further 15 minutes, and 12.1 g (0.05 mol) of 2,5-dimethyl-3-isoxazolidene-imine-hydroiodide are then added, care being taken to ensure that during the addition the temperature does not exceed 10°. The suspension is stirred at 20° for 1 hour; it is subsequently filtered, the filtrate is concentrated by evaporation, and the residue is distributed between chloroform and 2 N sodium hydroxide solution. The chloroform phase is washed with water until neutral, dried over sodium sulfate, and concentrated by evaporation to yield crude N-(2,5-dimethyl-3-isoxazolidinylidene)-N'-phenyl-1-pyrrolidinecarboximideamide. The crude maleate produced therefrom with maleic acid is purified by filtration through silica gel (particle size 0.063–0.2 mm) with a solvent mixture of chloroform and methanol (95:5). The pure N-(2,5-dimethyl-3-isoxazolidinylidene)-N'-phenyl-1-pyrrolidinecarboximide-amide-maleate melts at 112°-114° after recrystallisation from ethyl acetate.

EXAMPLE 19

A mixture of 3.6 g of N'-phenyl-1-(4-morpholinyl)-S-methyl-isothiourea-hydroiodide and 2 g of 2-amino-2-thiazoline in 30 ml of acetonitrile is refluxed for 8 hours. The solvent is evaporated off under reduced pressure; the residue is then rendered basic with alkali, and is extracted with methylene chloride. The crude base is chromatographed on silica gel in ethyl acetate, and the column is eluted with ethyl acetate containing increasing amounts of methanol. The later fractions yield on oily base, which is treated with hydrogen chloride in isopropanol to obtain 1-(4-morpholinyl)-N'-phenyl-N-(2-thiazolinyl)-formamidine-hydrochloride.

What is claimed is:

1. Guanidine derivatives of the formula

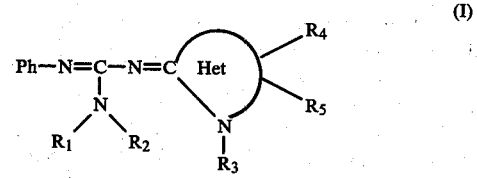

(I)

in which $R_1$ is an aliphatic radical which is unsubstituted or substituted by hydroxyl, lower alkanoyloxy, lower alkoxy, lower alkenoxy, halo, carboxy or lower alkoxycarbonyl, or is a cycloaliphatic radical which is unsubstituted or substituted by lower alkyl, $R_2$ is hydrogen or an aliphatic hydrocarbon radical which is unsubstituted or substituted by hydroxyl, lower alkanoyloxy, lower alkoxy, lower alkenoxy, halo, carboxy or lower alkoxycarbonyl, or $R_1$ and $R_2$ taken together are a lower alkylene chain which is uninterrupted or interrupted by oxygen, sulfur or nitrogen, which is unsubstituted or substituted by lower alkyl or phenyl, $R_3$ is hydrogen or lower alkyl, $R_4$ is hydrogen, lower alkyl, lower alkoxy, lower alkylthio, lower alkylamino, di-lower alkylamino, halo, trifluoromethyl, or phenyl which is unsubstituted or substituted by one to three identical or different lower aliphatic hydrocarbon radicals, hydroxy, mercapto, lower alkoxy, lower alkenoxy, lower alkylenedioxy, lower alkylthio halo trifluoromethyl, nitro, amino, lower alkylamino, di-lower alkylamino, carboxy or lower alkoxycarbonyl, or is, on a carbon atom which has single bonds on both sides, oxo, $R_5$ is hydrogen or lower alkyl, Het is isoxazolidine, and Ph is phenyl which is unsubstituted or substituted by one to three identical or different lower aliphatic hydrocarbon radicals, hydroxy, mercapto, lower alkoxy, lower alkenoxy, lower alkylenedioxy, lower alkylthio, halo, trifluoromethyl, nitro, amino, lower alkylamino, di-lower alkylamino, carboxy or lower alkoxycarbonyl, and also their tautomeric compounds and salts.

2. A compound as claimed in claim 1 corresponding to formula I, in which $R_1$ is lower alkyl or cycloalkyl and $R_2$ is hydrogen or lower alkyl, or $R_1$ and $R_2$ taken together are a lower alkylene chain which is uninterrupted or is interrupted by oxygen, sulfur or nitrogen which is unsubstituted or is substituted by lower alkyl or phenyl, and $R_4$ is hydrogen, lower alkyl, lower alkoxy, lower alkylthio, lower alkylamino, di-lower alkylamino, halo, trifluoromethyl or, on a carbon atom which has single bonds on both sides, also oxo, or phenyl which is unsubstituted or substituted by lower alkyl, lower alkoxy or halo.

3. A compound as claimed in claim 1 corresponding to formula I in which $R_1$ is lower alkyl and $R_2$ is hydrogen or lower alkyl or -$NR_1R_2$ is pyrrolidino, 2,5-dimethylpyrrolidino, piperidino, 2-methylpiperidino, hexahydroazepino, octahydroazocino, morpholino, thiomorpholino, piperazino or N-methyl- or N-phenyl-piperazino, $R_4$ is hydrogen, lower alkyl, lower alkoxy, lower alkylthio, lower alkylamino, di-lower alkylamino, halogen, trifluoromethyl or, on a carbon atom which has single bonds on both sides, also oxo, or phenyl which is unsubstituted or substituted by lower alkyl, lower alkoxy or halogen, $R_5$ is hydrogen or lower alkyl and Ph is a phenyl radical which is unsubstituted or substituted by lower alkyl, lower alkoxy or halogen.

4. A compound as claimed in claim 1 corresponding to formula I in which $R_1$ is lower alkyl and $R_2$ is hydrogen or lower alkyl, or the group -$NR_1R_2$ is pyrrolidino, 2,5-dimethylpyrrolidino, piperidino, 2-methyl-piperidino or morpholino, $R_4$ is hydrogen, lower alkyl, lower alkoxy, lower alkylthio, halogen, trifluoromethyl or, on a carbon atom which has single bonds on both sides, also oxo, or phenyl which is unsubstituted or substituted by lower alkyl, lower alkoxy or halogen, $R_5$ is hydrogen or lower alkyl, and Ph is a phenyl radical which is unsubstituted or substituted by lower alkyl, lower alkoxy or halogen.

5. A compound as claimed in claim 1 corresponding to formula I in which $R_1$ is methyl or ethyl, and $R_2$ is hydrogen, methyl or ethyl, or the group -$NR_1R_2$ is pyrrolidino, piperidino or morpholino, $R_3$ is hydrogen, methyl or ethyl, $R_4$ is hydrogen, methyl or ethyl, methoxy or ethoxy, methylthio or ethylthio, chlorine or bromine, trifluoromethyl or phenyl which is unsubstituted or substituted by methyl or ethyl, chlorine or bromine, $R_5$ is hydrogen, methyl or ethyl, and Ph is a phenyl radical which is unsubstituted or substituted by methyl or ethyl, chlorine, bromine, methoxy or ethoxy.

6. A compound as claimed in claim 1 and being N-(2,5-dimethyl-3-isoxazolidinylidene)-N'-phenyl-4-morpholine-carboximide and a therapeutically useful salt thereof.

7. A compound as claimed in claim 1 and being N-(2,5-dimethyl-3-isoxazolidinylidene)-N'-phenyl-1-piperidine-carboximide-amide and a therapeutically useful salt thereof.

8. A compound as claimed in claim 1 and being N-(2-methyl-3-isoxazolidinylidene)-N'-phenyl-4-morpholine-carboxamide-amide and a therapeutically useful salt thereof.

9. A compound as claimed in claim 1 and being N-(2,5,5-trimethyl-3-isoxazolidinylidene)-N'-phenyl-4-morpholine-carboximide-amide and a therapeutically useful salt thereof.

10. A compound as claimed in claim 1 and being N-(2,5-dimethyl-3-isoxazolidinylidene)-N'-phenyl-1-pyrrolidine-carboximide-amide and a therapeutically useful salt thereof.

11. A therapeutic composition for the treatment of hyperglycaemia comprising an effective amount of an hypoglycaemic active compound of formula I as claimed in claim 1 together with a pharmaceutically acceptable excipient.

12. A therapeutic composition as defined in claim 11, wherein the hypoglycaemic active compound is N-(2,5-dimethyl-3-isoxazolidinylidene)-N'-phenyl-4-morpholine-carboximide-amide.

13. A method for the treatment of hyperglycaemia which comprises administering to a living body suffering from hyperglycaemia an effective amount of a compound of formula I as claimed in claim 1.

* * * * *